United States Patent [19]
Meirowitz et al.

[11] Patent Number: 5,458,963
[45] Date of Patent: *Oct. 17, 1995

[54] NONWOVEN WEB CONTAINING SHAPED FIBERS

[75] Inventors: Randy E. Meirowitz, Neenah; Jerome W. Riese; Robert J. Phelan, both of Appleton, all of Wis.

[73] Assignee: Kimberly-Clark Corporation, Neenah, Wis.

[*] Notice: The term of this patent shall not extend beyond the expiration date of Pat. No. 5,314,743.

[21] Appl. No.: 341,279

[22] Filed: Nov. 16, 1994

Related U.S. Application Data

[63] Continuation of Ser. No. 206,981, Mar. 4, 1994, abandoned, which is a continuation of Ser. No. 628,782, Dec. 17, 1990, Pat. No. 5,314,743.

[51] Int. Cl.⁶ ............................................. B32B 5/06
[52] U.S. Cl. ........................... 428/297; 428/221; 428/224; 428/284; 428/298; 428/400; 428/913; 604/358; 604/378
[58] Field of Search ................................ 428/221, 224, 428/284, 297, 298, 400, 913; 604/358, 378

[56] References Cited

U.S. PATENT DOCUMENTS

| | | | |
|---|---|---|---|
| Re. 31,380 | 9/1983 | Smith | 106/164 |
| 2,336,743 | 12/1943 | Manning | 18/8 |
| 2,945,739 | 7/1960 | Lehmicke | 18/54 |
| 3,169,899 | 2/1965 | Steuber | 161/72 |
| 3,276,944 | 10/1966 | Levy | 161/150 |
| 3,314,840 | 4/1967 | Lloyd et al. | 156/167 |
| 3,368,934 | 2/1968 | Vosburgh, Sr. | 161/150 |
| 3,509,009 | 4/1970 | Hartmann | 161/150 |

(List continued on next page.)

FOREIGN PATENT DOCUMENTS

| | | |
|---|---|---|
| 0301874 | 2/1989 | European Pat. Off. |
| 0391814 | 10/1990 | European Pat. Off. |
| 2588285 | 4/1987 | France |
| 54-138617 | 10/1979 | Japan |
| 62-53605 | 11/1987 | Japan |
| 63-227871 | 9/1988 | Japan |
| 6-200408 | 7/1994 | Japan |
| 2085304 | 4/1982 | United Kingdom |
| 2208277 | 3/1989 | United Kingdom |
| 2215609 | 9/1989 | United Kingdom |
| WO90/12130 | 10/1990 | WIPO |
| WO91/12949 | 9/1991 | WIPO |
| WO93/02235 | 2/1993 | WIPO |
| WO93/01779 | 2/1993 | WIPO |
| WO93/01780 | 2/1993 | WIPO |
| WO93/01781 | 2/1993 | WIPO |
| WO93/01782 | 2/1993 | WIPO |
| WO93/01783 | 2/1993 | WIPO |
| WO93/01784 | 2/1993 | WIPO |
| WO94/05245 | 3/1994 | WIPO |

OTHER PUBLICATIONS

An article entitled "A Simplified Thermodynamic Approach to Capillarity—I. Application to Flow in Capillary Channels" by Anthony M. Schwartz & Francis W. Minor, *Journal of Colloid Science*, vol. 14, pp. 572–583 (1959).

A sales brochure of Spinnerettes from Nippon Nozzle Co. Ltd.

Communication—European Search Report—EP 91 12 1370.

*Primary Examiner*—James J. Bell
*Attorney, Agent, or Firm*—Thomas J. Mielke; John R. Schenian

[57] ABSTRACT

A nonwoven web for absorbing and transporting a liquid, which web is capable of both interfiber and intrafiber liquid transportation. The web includes shaped fibers, which fibers define a notch, which notch defines an angle alpha such that α<180°−2θ wherein θ is the contact angle between said liquid and the shaped fiber. The nonwoven web further includes high-absorbency material in fluid communication with said nonwoven web in an area wherein intrafiber liquid transport occurs.

22 Claims, 6 Drawing Sheets

U.S. PATENT DOCUMENTS

| | | | |
|---|---|---|---|
| 3,554,854 | 1/1971 | Hartmann | 161/150 |
| 3,630,816 | 12/1971 | Parker | 161/72 |
| 3,670,069 | 6/1972 | Mitchell et al. | 264/187 |
| 3,865,918 | 2/1975 | Mitchell et al. | 264/188 |
| 3,984,515 | 10/1976 | Mommaerts et al. | 264/182 |
| 4,129,679 | 12/1978 | Woodings | 428/398 |
| 4,144,079 | 3/1979 | Smith | 106/164 |
| 4,179,259 | 12/1979 | Belitsin et al. | 425/461 |
| 4,213,459 | 7/1980 | Sigl et al. | 128/287 |
| 4,360,022 | 11/1982 | Usami et al. | 128/290 R |
| 4,468,428 | 8/1984 | Early et al. | 428/221 |
| 4,469,746 | 9/1984 | Weisman et al. | 428/289 |
| 4,668,566 | 5/1987 | Braun | 428/286 |
| 4,699,619 | 10/1987 | Bernardin | 604/378 |
| 4,710,187 | 12/1987 | Boland et al. | 604/385 A |
| 4,753,834 | 6/1988 | Braun et al. | 428/74 |
| 4,762,521 | 8/1988 | Roessler et al. | 604/38 SA |
| 4,770,656 | 9/1988 | Proxmire et al. | 604/393 |
| 4,778,460 | 10/1988 | Braun et al. | 604/380 |
| 4,781,962 | 11/1988 | Zammarripa et al. | 428/138 |
| 4,783,231 | 11/1988 | Raley | 156/167 |
| 4,798,603 | 1/1989 | Meyer et al. | 604/378 |
| 4,885,202 | 12/1989 | Lloyd et al. | 428/171 |
| 4,944,735 | 7/1990 | Mokry | 604/385.2 |
| 5,006,057 | 4/1991 | Bagrodia et al. | 425/464 |
| 5,200,248 | 4/1993 | Thompson et al. | 428/131 |
| 5,281,208 | 1/1994 | Thompson et al. | 604/378 |
| 5,314,743 | 5/1994 | Meirowitz et al. | 428/297 |
| 5,342,336 | 8/1994 | Meirowitz et al. | 604/378 |

NONWOVEN WEB CONTAINING SHAPED FIBERS

This is a continuation of application Ser. No. 08/206,981, filed on Mar. 4, 1994, now abandoned, which in turn is a continuation of Ser. No. 07/628,782, filed Dec. 17, 1990, now U.S. Pat. No. 5,314,743.

BACKGROUND OF THE INVENTION

1. Field of the Invention

The present invention relates to nonwoven webs. Specifically, the present invention relates to nonwoven webs comprising shaped fibers and a high-absorbency material in fluid communication with said nonwoven web.

2. Description of the Related Art

The use of shaped fibers to form various woven and nonwoven products is known. For example, U.S. Pat. No. 4,129,679 issued Dec. 12, 1978, to Woodings describes regenerated cellulose filaments having a collapsed hollow structure and a multi-limbed cross section. The fibers are said to possess a high capability of water imbibition. The fibers can be formed into woven fabrics like toweling and non-woven fabrics and wadding such as diapers, sanitary napkins, tampons and swabs.

European Patent Application 0 301 874 published Feb. 1, 1989, is directed to cellulosic fibers having a decitex of less than 5.0 and a multi-limbed cross section. The limbs have a length-to-width aspect ratio of at least 2:1. The fibers can be formed into woven, nonwoven, or knitted fabrics and are described as being especially useful for absorbent products.

Similarly, Japanese Kokoku Patent No. SHO 62[1987]-53605 published Nov. 11, 1987, is directed to synthetic fibers having shaped cross sectional views meeting certain criteria. Again, the fibers are said to have excellent water absorptivity when formed into nonwoven products.

When nonwoven webs are employed in disposable absorbent products such as diapers, training pants, adult incontinent products, feminine care products, wound dressings, and the like, the simple ability to absorb a liquid is generally not sufficient to ensure optimum performance in a product. For example, during use, many personal care products are exposed to multiple insults of a liquid. In order to ensure proper absorption of subsequent insults, it is generally desired that the first insult of liquid be not only absorbed but also transported within the absorbent products to areas remote from the point of insult.

Additionally, the ability of a nonwoven web to transport a liquid is desirable for another reason. Specifically, when the nonwoven web is to be employed in an absorbent product, it is often desirable to incorporate into the nonwoven web a high-absorbency material. Such high-absorbency materials are known to those skilled in the art and are generally capable of absorbing many times their weight in a liquid. Thus, much of the total absorbent capacity of an absorbent product, employing such high-absorbency materials, results from the presence of the high-absorbency material. In order for the high-absorbency material to absorb a liquid, the liquid must come into contact with the high-absorbency material. If the nonwoven web incorporating the high-absorbency material is not able to transport a liquid from the point of liquid application, all of the high-absorbency material must be placed in the general area where the liquid to be absorbed will be applied to the nonwoven web. This is not always desirable.

Specifically, when a high concentration of a high-absorbency material is localized in a nonwoven web, it is possible for gel blocking to occur. That is, the high-absorbency material can swell in the localized area to the extent that an essentially liquid-impermeable mass of high-absorbency material is formed. Should this occur, subsequent insults cannot be absorbed by the nonwoven web. Accordingly, it is often desirable to more evenly distribute the high-absorbency material in the nonwoven web. For this reason, it is desirable for the nonwoven web to be able to transport a liquid from a point of application to a high-absorbency material located remote from the point of application.

In the past, the ability of a nonwoven web to transport a liquid was generally regulated by adjusting the capillary size of the nonwoven web. Specifically, loosely compacted, relatively low density nonwoven webs were generally not capable of good liquid transport against a pressure, such as a gravitational head, due to the relatively large pore size present within the webs and the correspondingly relatively low capillary pressure. In order to obtain good liquid transport against a pressure, it was generally believed necessary to densify the nonwoven webs to reduce the capillary pore size thereby increasing the capillary pressure and allowing the liquid to be transported farther against a pressure from the point of application. Unfortunately, as a general rule, the higher the density of a nonwoven web, the less able the nonwoven web is to rapidly accept a liquid applied thereto.

When nonwoven webs are employed in absorbent products, it is desirable that the web not only be able to transport a liquid against a pressure but also be able to quickly accept a liquid. Therefore, in order to provide a structure capable of both quickly accepting a liquid and of transporting the liquid against a pressure, it was often thought necessary to provide two layers; one of a relatively loosely compacted, porous nature, able to quickly accept a liquid, and one of a higher density, compacted nature, capable of transporting the liquid against a pressure.

SUMMARY OF THE INVENTION

It is desirable to provide a nonwoven web capable of both absorbing a liquid applied thereto and of transporting a liquid against a pressure to points remote from the point of liquid application which ability to transport a liquid is not solely dependent on the capillary pore size (density) of the nonwoven web.

These and other related goals are achieved in a nonwoven web for absorbing and transporting a liquid, said web being capable of interfiber and intrafiber liquid transport. In one embodiment, the web comprises a shaped fiber which shaped fiber defines a notch. The notch defines an angle alpha ($\alpha$) such that:

$$\alpha < 180° - 2\theta$$

wherein $\theta$ is the contact angle between said liquid and the shaped fiber. The nonwoven web further comprises a high-absorbency material in liquid communication with an area of intrafiber liquid transport.

DETAILED DESCRIPTION OF THE PREFERRED EMBODIMENTS

The present invention relates to a nonwoven web for absorbing and transporting a liquid. The nonwoven web is capable of interfiber liquid transport as well as intrafiber liquid transport.

As used herein, reference to interfiber liquid transport refers to the situation wherein a liquid moves through a nonwoven web of fibers as a result of capillaries formed by said fibers. Those skilled in the art will recognize that the vertical distance of interfiber liquid transport depends on the capillary pressure of the system. The capillary pressure of a cylindrical capillary is expressed by the equation:

$$P = \frac{2\gamma \cos\theta}{r}$$

wherein P is the capillary pressure, $\gamma$ is the surface tension of the liquid, $\theta$ is the liquid-fiber contact angle, and r is the capillary radius. With a given liquid, the capillary pressure (capillary force) increases with the cosine of the liquid-fiber contact angle and decreases with larger capillary radii so that smaller capillaries will transport a liquid farther vertically through the interfiber capillaries or against a pressure.

As used herein, intrafiber liquid transport refers to the situation wherein a liquid is transported against a pressure along the length of an individual fiber as a result of a notch or channel defined by the surface of the individual fiber. Exemplary of pressures against which the liquid may be transported are gravity, capillary pressure differentials, and the like.

Figure 1:
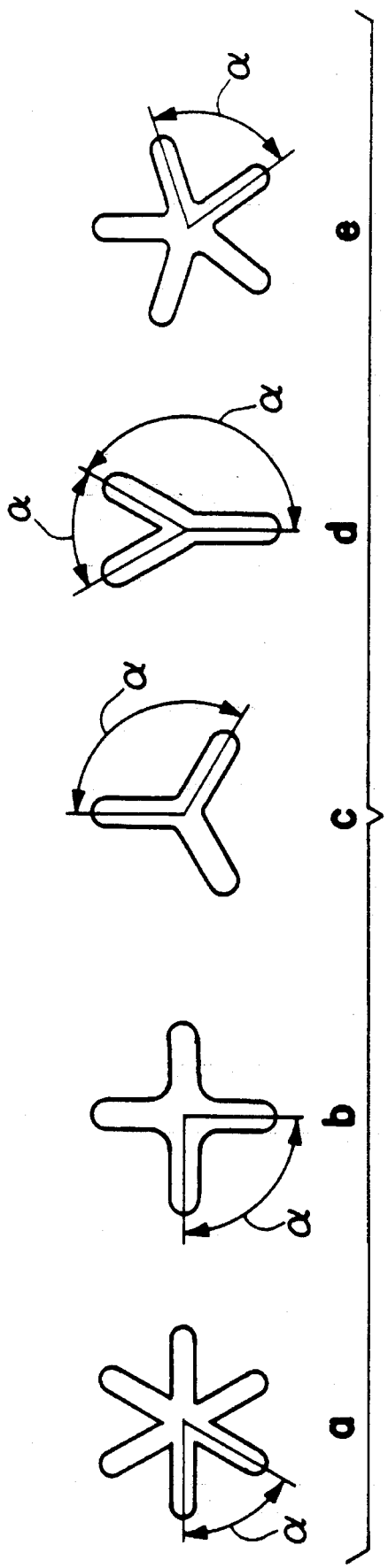
FIG. 1 is a cross-sectional drawing of shaped fibers according to the present invention.

In one embodiment, the nonwoven webs of the present invention comprise a shaped fiber, the shaped fiber defines a notch, the notch defines an angle alpha ($\alpha$). With reference to FIG. 1, a variety of cross sectional views of shaped fibers believed suitable for use in the present invention are illustrated. As can be seen from reference to FIG. 1a–e, the illustrated shaped fibers all define one or more angles alpha. The angles alpha defined by an individual fiber may be the same as in FIG. 1b, or may be different as in FIG. 1d.

Applicants have discovered that in order to provide a shaped fiber capable of intrafiber liquid transport, the shaped fiber suitably defines a notch, which notch defines an angle alpha ($\alpha$) such that:

$$\alpha < 180° - 2\theta$$

wherein $\theta$ is the contact angle between a liquid to be transported and the shaped fiber.

As used herein, reference to the contact angle of the liquid to be absorbed and transported and the material from which the shaped fibers are formed is determined as set forth by Good and Stromberg in "Surface and Colloid Science" Vol. II (Plenum Press, 1979). Additionally, the angle alpha defined by the notch defined by the shaped fiber is suitably measured by scanning electron microscopy, optical microscopy, or other methods known to those skilled in the art.

Figure 2:
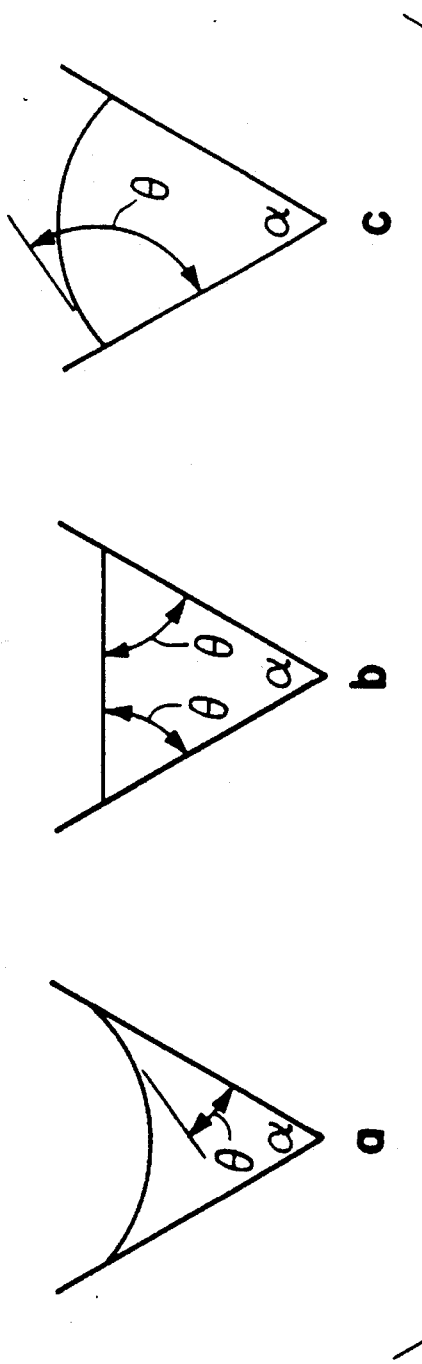
FIG. 2 represents various contact angles between shaped fibers and a liquid present in the shaped fibers.

The conditions for intrafiber liquid transport are explained in greater detail in connection with FIG. 2. In FIG. 2a–c, an enlarged notch is shown. The notches (2a–c) all define the same angle alpha. Each of the notches 2a–c is shown containing a liquid having a different liquid/fiber contact angle, in air, of $\theta$. In FIG. 2a, the liquid meniscus in the notch appears concave outward and illustrates the situation wherein $\alpha < 180° - 2\theta$. In FIG. 2b, the liquid meniscus forms a straight line in the notch and illustrates the situation wherein $\alpha = 180° - 2\theta$. In FIG. 2c, the liquid meniscus appears convex outward and illustrates the situation wherein $\alpha > 180° - 2\theta$.

Intrafiber liquid transport (wicking) according to the present invention occurs in the situation illustrated in FIGS. 2a and does not occur in the situations illustrated in FIG. 2b or 2c. The ability of a notch defined by a shaped fiber to provide intrafiber wicking can be controlled by either changing the contact angle $\theta$ of the liquid to be transported or by changing the angle alpha defined by the notch. So long as the angle alpha defined by the notch meets the requirement that; $\alpha < 180° - 2\theta$, the fiber is capable of intrafiber transport of the liquid.

Figure 3:
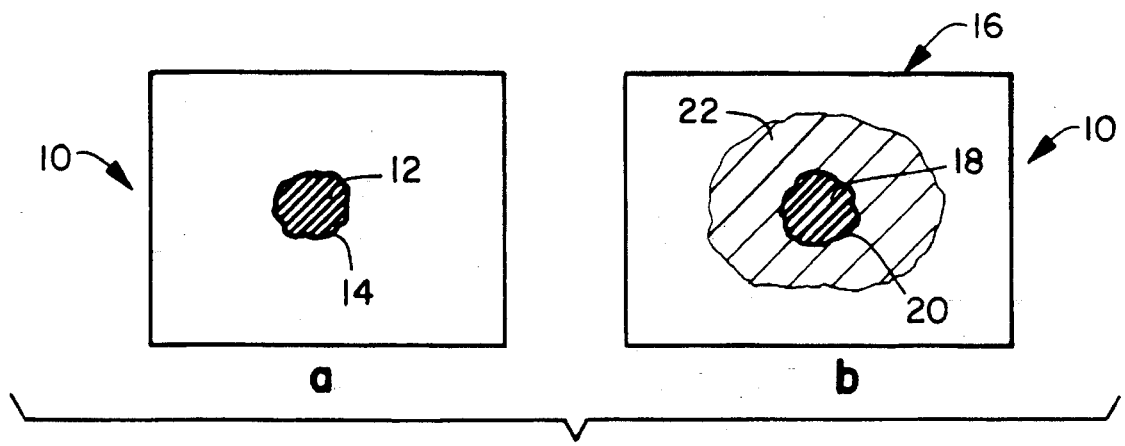
FIG. 3 illustrates liquid applied to a nonwoven web.

FIG. 3a illustrates a nonwoven web 10 formed from shaped fibers, which fibers define a notch, defining an angle alpha, wherein the angle $\alpha > 180° - 2\theta$. Accordingly, when a liquid 12 is applied to a point on the surface of the nonwoven web 10, the nonwoven web 10 is only capable of interfiber liquid transport. That is, the liquid 12 is transported in the capillaries defined by the fibers forming the nonwoven web and is transported to form an area of interfiber liquid transport 14 illustrated by the dark circle in FIG. 3a. The size of the interfiber liquid transport area 14 will depend on the amount of liquid applied, and the capillary pressure of the system which is, as discussed above, dependent on capillary radius, surface tension of the liquid 12, and contact angle $\theta$ between the fibers and the liquid 12.

FIG. 3b illustrates a nonwoven web 16 according to the present invention. Specifically, nonwoven web 16 is formed from shaped fibers defining a notch, which notch defines an angle alpha wherein $\alpha < 180° - 2\theta$. With reference to FIG. 3b, it is seen that when liquid 18 is applied to a point on the surface of the nonwoven web 16, the nonwoven web 16 transports the liquid in the interfiber capillaries to form an area of interfiber liquid transport 20. As explained in connection with FIG. 3a, the size of interfiber liquid transport area 20 depends on the capillary pressure which, in turn, depends on the capillary radius, surface tension of the liquid, and contact angle of the liquid and the fiber material. After the liquid 18 is transported through interfiber liquid transport, the capillaries of interfiber transport area 20 are essentially filled with the liquid 18. Thus, the liquid 18 is in contact with the notches defined by the shaped fibers. Since the shaped fibers are capable of intrafiber transport, liquid in contact with the notches is transported in the notches to form an area of intrafiber liquid transport 22. The size of intrafiber liquid transport 22 is dependent on the amount of liquid contained in the capillaries of the interfiber liquid transport area 20 and the amount of liquid maintained in the notches defined by the shaped fibers. Intrafiber liquid transport can continue until the capillaries of interfiber liquid transport area 20 are essentially void of liquid.

Figure 4:
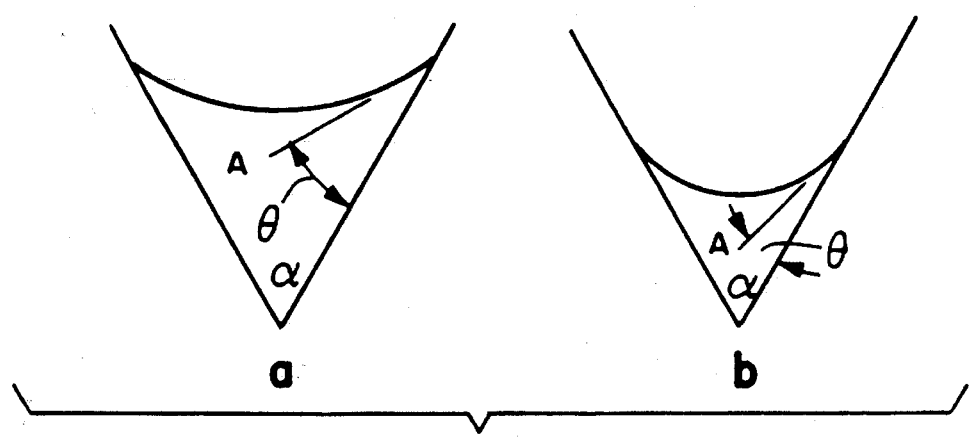
FIG. 4 represents a liquid present in shaped fibers accord-

The amount of liquid present within the notch during intrafiber liquid transport is believed to be dependent on the capillary pressure of the capillary from which the fiber is drawing the liquid which is being transported. With reference to FIG. 4, as the cross sectional area A of the liquid present in a notch defined by a shaped fiber decreases, the capillary pressure of said liquid increases. In order to achieve intrafiber liquid transport, the capillary pressure of the liquid in the notch of the shaped fiber must be greater than the capillary pressure of the interfiber capillary from which the liquid is being drawn. In the instant case, the amount of liquid present in the notch during intrafiber liquid transport, as measured by the cross sectional area A of the liquid in the notch, is dependent on the capillary pressure of the liquid in the interfiber capillary from which the notch is drawing the liquid. Thus, the amount of liquid present in the notch of the shaped fiber will decrease until the capillary pressure of the liquid present in the notch is greater than the capillary pressure of the capillary from which the liquid is being drawn. That is, the amount of liquid present in the notch of the shaped fiber of the present invention can self adjust such that the capillary pressure of the liquid in the notch is greater than the capillary pressure of the interfiber capillary from which the liquid is drawn.

With reference to FIGS. 4a and b, if the capillary from which the fluid is drawn is relatively large (relatively low capillary pressure), the amount of liquid present in the notch of the shaped fiber can be relatively large as represented by FIG. 4a. If, however, the capillary from which the fluid is drawn is relatively small (relatively high capillary pressure), the amount of liquid present in the notch of the shaped fiber will be relatively small as indicated by FIG. 4b. Nonetheless, in both cases, the capillary pressure of the liquid present in the notch, in the area of intrafiber liquid transport, is greater than the capillary pressure of the capillary in the area of interfiber liquid transport from which the fiber draws the liquid.

The shaped fibers can be formed from any material capable of forming a nonwoven web, and defining a notch defining an angle as described above. As a general rule, the shaped fibers are formed from a cellulose derivative such as rayon or cellulose acetate or from a synthetic polymeric material such as polyolefins, polyesters, polyamides, polyurethanes, and the like. The materials from which the shaped fiber can be formed may be either hydrophilic or hydrophobic. As used herein, "hydrophilic" refers to fibers having a water-in-air contact angle of less than 90° as determined as set forth by Good and Stromberg in "Surface and Colloid Science" Vol. II, (Plenum Press, 1979). "Hydrophobic" refers to fibers having a water-in-air contact angle greater than 90° as determined as set forth by Good and Stromberg in "Surface and Colloid Science" Vol. II, (Plenum Press, 1979). When the shaped fibers are formed from hydrophobic material, the fibers must be treated to provide them with a hydrophilic surface. This is necessary since hydrophobic fibers cannot meet the requirement of $\alpha < 180° - 2\theta$ if $\theta$ is greater than 90°. Methods of providing hydrophobic materials with a hydrophilic surface are known. Exemplary of such a method is the application of a surfactant or other hydrophilizing agent to the fibers.

Similarly, if a hydrophilic polymer having a contact angle of less than 90° is desired to be rendered more hydrophilic to thereby decrease its contact angle with respect to a given liquid, it is possible to treat the hydrophilic material with a surfactant or other hydrophilizing agent to impart a more hydrophilic surface. The hydrophilizing treatment may be either fugitive or nonfugitive with respect to the shaped fiber.

Methods of forming shaped fibers are known to those skilled in the art. As a general rule, shaped fibers formed from a synthetic polymeric material are generally prepared by extruding the fibers through a die orifice generally corresponding to the desired shape. Such a method is described in U.S. Pat. No. 2,945,739 issued Jul. 19, 1960, to Lehmicke, or in Japanese Kokoku Patent No. SHO 62[1987]-53605. If the shaped fiber is to be formed from a cellulosic derivative, such as rayon, the shaped fibers can be formed from conventional viscose and are conveniently spun from standard viscose compositions using standard viscose spinning conditions; with the exception that shaped extrusion holes in the spinneret are substituted for the conventional circular shaped holes. Such a method is described in European Patent Application 0 301 874 published Feb. 1, 1989. Alternatively, the shaped fiber may be formed from cellulose acetate. For example, Y-shaped cellulose acetate fibers, commercially available from Hoechst-Cellanese Corporation, Narrows, Va., under the trade designation Cellulose Acetate Tow, have been found suitable for use in the present invention. Further, the shaped fiber may be formed by twisting two fibers together. The twisting of the two fibers forms a helical notch which may be capable of intrafiber liquid transport.

The shaped fibers according to the present invention generally have a diameter of from about 0.25 micrometer to about 500 micrometers, preferably of from about 0.5 micrometer to about 40 micrometers.

The shaped fibers employed in the nonwoven webs according to the present invention define at least one notch, which notch defines an angle alpha as described above. As can be seen from reference to FIG. 1, shaped fibers suitable for use in the present invention may have a variety of cross-sectional shapes and often define more than one notch. The fibers may define two, three, or more notches. Each notch may have generally the same angle alpha or may define notches having several different angles. As a general rule, it is preferred that the shaped fibers employed in forming the nonwoven web of the present invention define two, preferably three, and most preferably at least four notches, which notches define an angle alpha as described above.

Nonwoven webs according to the present invention can suitably be formed in any manner capable of forming nonwoven webs known to those skilled in the art. For example, the nonwoven web may be formed through a carding process, rando process, spundbond process, needlepunch process, and the like. The nonwoven webs according to the present invention suitably have a density of from about 0.01 gram per cubic centimeter to about 0.5 gram per cubic centimeter, preferably of from about 0.05 gram per cubic centimeter to about 0.2 gram per cubic centimeter, and a thickness of from about 0.5 micrometer to about 0.05 meter, preferably from about 50 micrometers to about 0.015 meter.

Not all of the fibers from which the nonwoven web according to the present invention is formed need to be shaped fibers defining a notch defining an angle alpha as described above. Nonetheless, as a general rule, it is desired that at least about 25 weight percent, beneficially at least about 50 weight percent, preferably at least about 90 weight percent, and most preferably about 100 weight percent, based on the total weight of fibers present in the nonwoven web, comprise a shaped fiber defining a notch, which notch defines an angle alpha such that $\alpha < 180° - 2\theta$, wherein $\theta$ is the contact angle between the fibers and the liquid.

In addition to shaped fibers defining a notch, which defines an angle as described above, the nonwoven webs according to the present invention may comprise up to about 75 weight percent, based on total weight of fibers present in the nonwoven web, of a fiber which either defines no notch or which defines a notch which notch does not define an angle alpha meeting the requirements discussed above. The amount of shaped fibers as well as the number of notches defining an angle alpha such that α<180°−2θ, directly affects both the amount and speed with which intrafiber liquid transport occurs. For this reason, it is preferred that generally all of the fibers present in the nonwoven web are shaped fibers defining a notch which defines an angle alpha such that α<180°−2θ.

The nonwoven webs according to the present invention comprise a high-absorbency material. The high-absorbency material is in liquid communication with the nonwoven web in an area of intrafiber liquid transport such as area 22 as illustrated in FIG. 3b. As used herein, a high-absorbency material will be considered to be in liquid communication with the nonwoven web, in an area of intrafiber liquid transport, when a liquid present in the area of intrafiber liquid transport can flow into contact with the high-absorbency material.

For example, the high-absorbency material may be present in the web in the area of intrafiber liquid transport 22 illustrated in FIG. 3b. Alternatively, the high-absorbency material may be present in a pouch or a second web which pouch or web is, in turn, in contact with the area of intrafiber liquid transport. The high-absorbency material may be in liquid communication with the nonwoven web in an area of interfiber liquid transport such as area 20 illustrated in FIG. 3b, or may only be in liquid communication with the nonwoven web in an area of intrafiber fluid transport.

Applicants have discovered that, when the high-absorbency material is in liquid communication with the nonwoven web in an area of intrafiber liquid transport, the high-absorbency material may contact the liquid transported by the notches. When the high-absorbency material is in contact with the liquid in an area of intrafiber liquid transport, the high-absorbency material is able to absorb the liquid, thus improving utilization of the high-absorbency material and allowing continued intrafiber liquid transport. For example, Applicants have found that, when a high-absorbency material capable of, for example, absorbing twenty times its weight in a liquid is in contact with the liquid in the area of intrafiber liquid transport, the shaped fiber will continue to transport liquid to the high-absorbency material until the absorption capacity of the high-absorbency material is reached or until there is no more available liquid for the shaped fiber to transport. This phenomenon is important for several reasons.

Intrafiber liquid transport allows for improved utilization of high-absorbency material present in or in liquid communication with the nonwoven web. That is, it is possible to disperse a given amount of high-absorbency material in the nonwoven web (or in liquid communication with the nonwoven web) over a greater area when intrafiber liquid transport occurs than when intrafiber liquid transport does not occur.

For example, if a given amount of high-absorbency material present in a nonwoven web is to be fully utilized in the nonwoven web, all of the high-absorbency material must be located in the area of interfiber liquid transport (such as area 20 in FIG. 3b) if only interfiber liquid transport occurs. However, when intrafiber liquid transport occurs, the same amount of high-absorbency material can be dispersed over a greater area (interfiber liquid transport area 20 and intrafiber liquid transport area 22 in FIG. 3b) and yet all of the high-absorbency material may contact the liquid to be absorbed. This allows a less dense concentration of high-absorbency material in the nonwoven web while maintaining the total absorbent capacity of the web. This is desirable since high density concentrations of certain high-absorbency materials tend to result in gel blocking wherein the interfiber capillaries become plugged with swollen high-absorbency material, thus preventing the maximum degree of interfiber liquid transport.

High-absorbency materials suitable for use in the present invention include both inorganic and organic high-absorbency materials. Suitable inorganic high-absorbency materials include, for example, absorbent clays and silica gels. Organic high-absorbency materials can include natural materials, such as agar, pectin, guar gum, and peat moss, as well as synthetic materials, such as synthetic hydrogel polymers. Such hydrogel polymers include, for example, carboxymethylcellulose, alkali metal salts of polyacrylic acids, polyacrylamides, polyvinyl alcohol, ethylene maleic anhydride copolymers, polyvinyl ethers, hydroxypropylcellulose, polyvinyl morpholinone, polymers and copolymers of vinyl sulfonic acid, polyacrylates, polyacrylamides, polyvinyl pyridine, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water-insoluble. Cross-linking may, for example, be by irradiation or by covalent, ionic, Van der Waals, or hydrogen bonding. Suitable high-absorbency materials are available from various commercial vendors such as the Dow Chemical Company, Cellanese Corporation, Allied-Colloid, and Stockhausen. Typically, the high-absorbency material is capable of absorbing at least about fifteen times its weight in water and preferably is capable of absorbing at least about 25–30 times its weight in water. The high-absorbency material can be present in the nonwoven web in an amount of from about 1 to about 95 weight percent, preferably of from about 5 to about 60 weight percent based on total weight of the nonwoven web.

Figure 5:
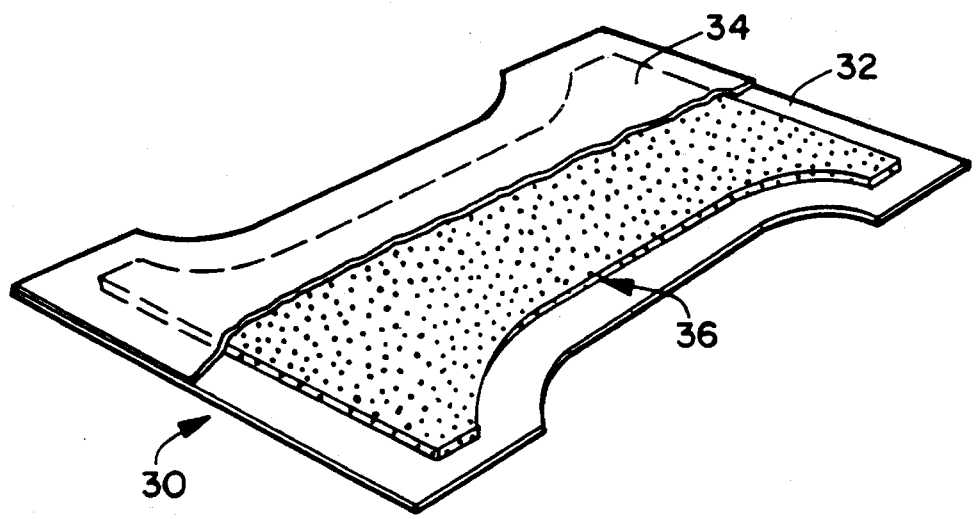
FIG. 5 illustrates a diaper according to the present invention.

The nonwoven webs according to the present invention are suitable for use in a variety of disposable absorbent products. For example, the nonwoven webs are suitable for use in personal care products such as diapers, adult incontinence products, feminine care products, training pants, wound dressings, and the like. With reference to FIG. 5, a suitable absorbent personal care product is a diaper 30 which comprises a fluid-impervious outer cover 32, fluid-pervious bodyside liner 34 adapted to contact the skin of a wearer and being superposed on said outer cover, and an absorbent structure 36 located between the bodyside liner and the fluid-impervious outer cover. The nonwoven webs according to the present invention may comprise the entire absorbent structure or may comprise one component of a multi-component absorbent structure. Exemplary of personal care products in which the nonwoven webs of the present invention may be employed are those described in U.S. Pat. Nos. 4,798,603 issued Jan. 7, 1989, to Meyer et al.; 4,710,187 issued Dec. 1, 1987, to Boland et al.; 4,770,656 issued Sep. 13, 1988, to Proxmire et al.; and 4,762,521 issued Aug. 9, 1988, to Roessler et al.

EXAMPLES

A carded web is prepared from 1.5 inch, 2.4 denier trilobal rayon staple fibers having a roughly Y-shaped cross section. The rayon fibers define 3 notches defining 3 angles alpha of about 120°. The carded web is prepared on a standard carding machine known to those skilled in the art. In general, the carding machine forms a web of deposited fibers and then combs the deposited fibers to impart some degree of orientation to the fibers.

As used herein, orientation of the fibers is expressed as a ratio of the machine direction strength to the cross direction strength of the carded web. Thus, a web which is 4 times stronger in the machine direction than in the cross direction is said, for the purposes of this application, to have a fiber orientation of 4:1. The strength of the web is determined according to methods known to those skilled in the art utilizing a device such as an Instron to determine tensile strength at break.

A control sample of a carded web is prepared from 3 denier rayon having a roughly circular cross section. Both carded webs are prepared to have a basis weight of about 1 oz/yd$^2$ and to possess the same machine direction:cross direction strength ratio. The machine direction:cross direction ratio is either 2:1 or 4:1. Again, as used herein, this ratio is believed to be indicative of the orientation of the fibers (2:1=twice as many fibers longitudinally oriented in the machine direction as in the cross direction).

The webs are then subjected to a horizontal wicking test wherein a 3 inch by 5 inch test sample of the web to be tested is placed on a horizontal polyester support web. Ten drops (about 0.05 milliliter per drop) of distilled water containing a nonsubstantive dye are then applied to a point on the web. A photograph showing fluid and fluid movement is taken initially (time=about 5 seconds) and after five minutes (time=5 minutes). The distilled water containing a nonsubstantive dye is found to have a contact angle theta ($\theta$) with the trilobal rayon fibers of less than 10° and with the round rayon fibers of less than 10°. Thus, it is seen that, for the trilobal fibers, $\alpha<180°-2\theta$. Different rayon fibers have different spin finishes on the fibers and thus may have different contact angles with a given liquid.

Figure 6:
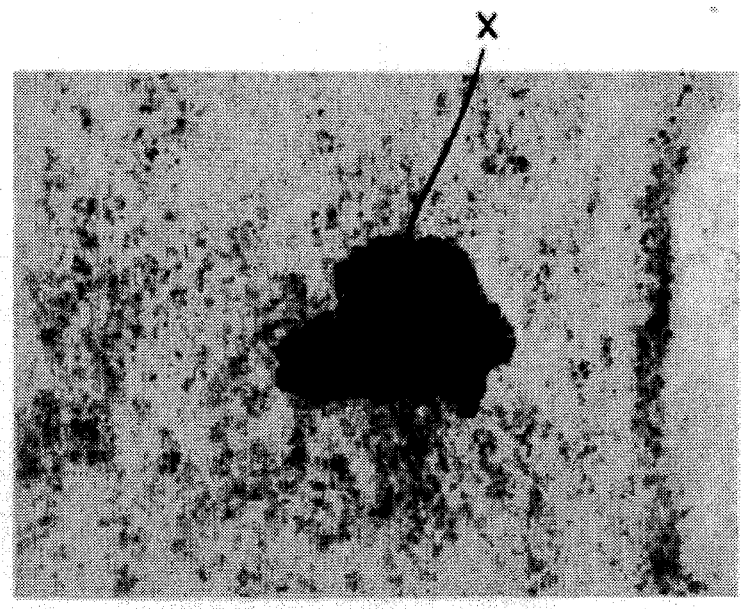
FIGS. 6–13 are photographs illustrating the liquid transport characteristics of several carded webs.

FIG. 6 is a photograph of a control web of 3 denier round rayon fibers with an orientation of 2:1 at time=5 seconds.

Figure 7:
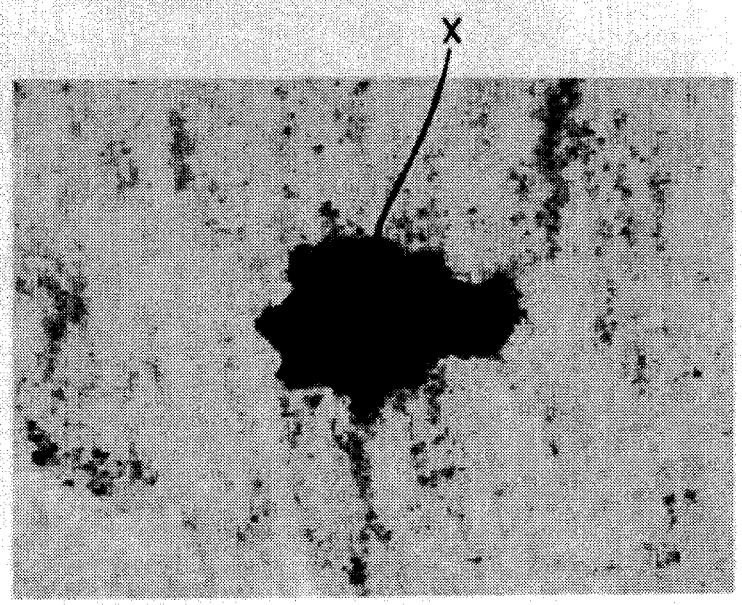

FIG. 7 is a photograph of a web of 2.4 denier trilobal rayon fibers with an orientation of 2:1 at time=5 seconds.

Figure 8:
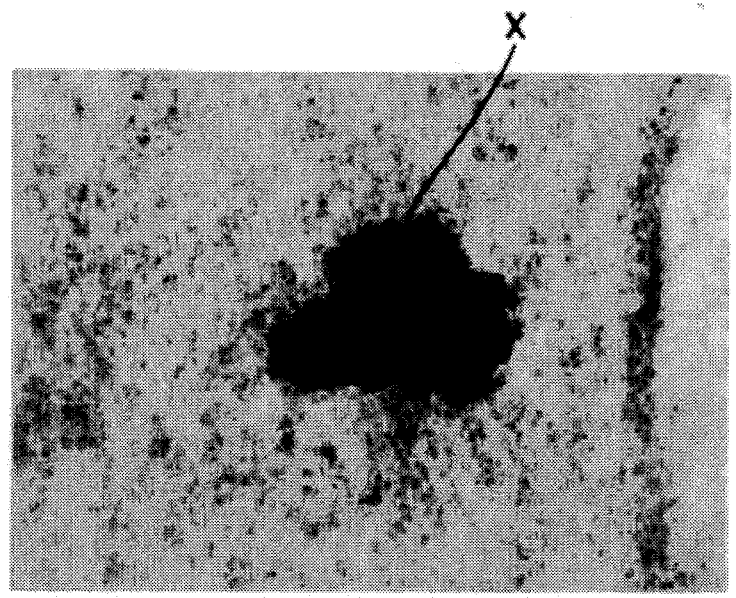

FIG. 8 is a photograph of the web of FIG. 6 at time=5 minutes.

Figure 9:
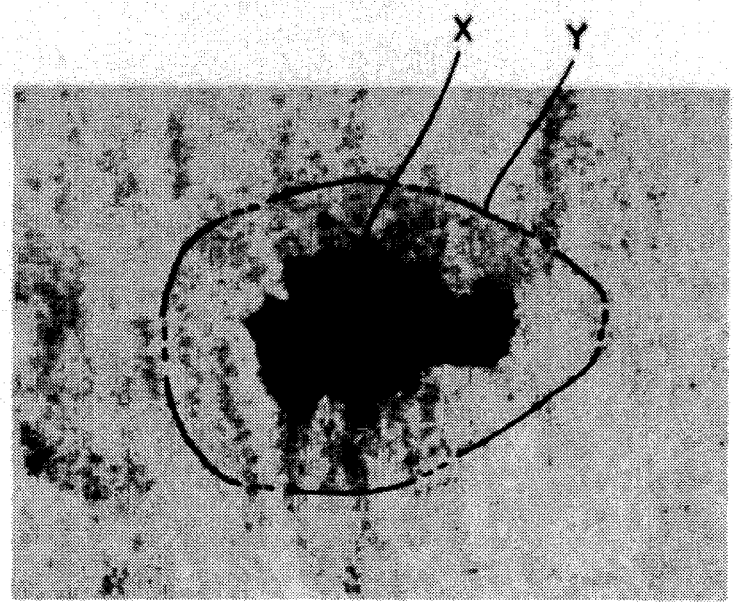

FIG. 9 is a photograph of the web of FIG. 7 at time=5 minutes.

Figure 10:
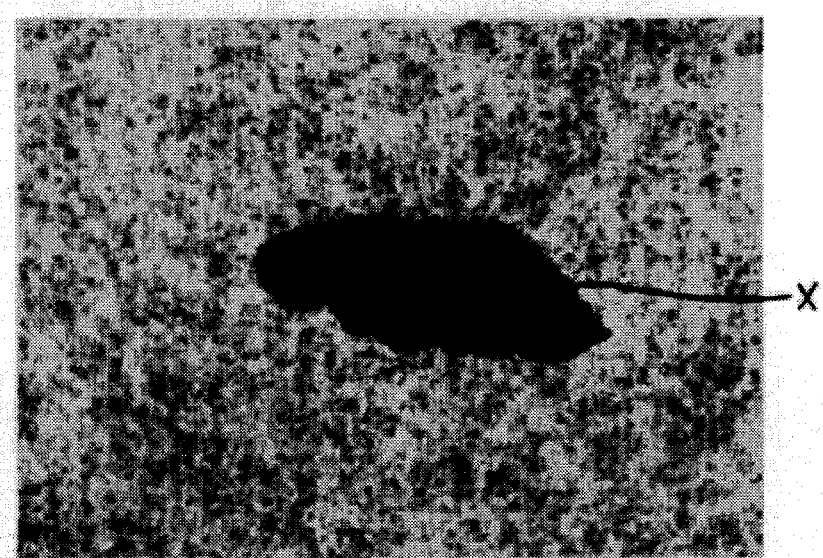

FIG. 10 is a photograph of a control web of 3 denier round rayon fibers with an orientation of 4:1 at time=5 seconds.

Figure 11:
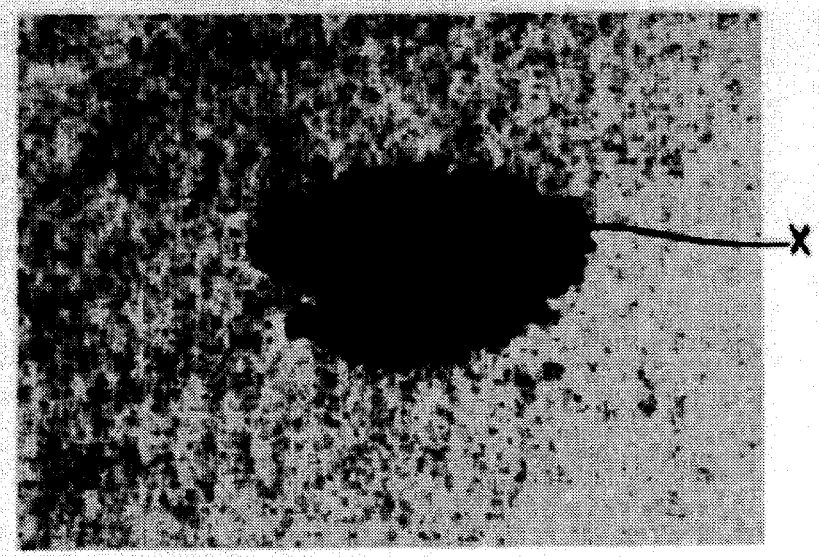

FIG. 11 is a photograph of a web of 2.4 denier trilobal rayon fibers with an orientation of 4:1 at time=5 seconds.

Figure 12:
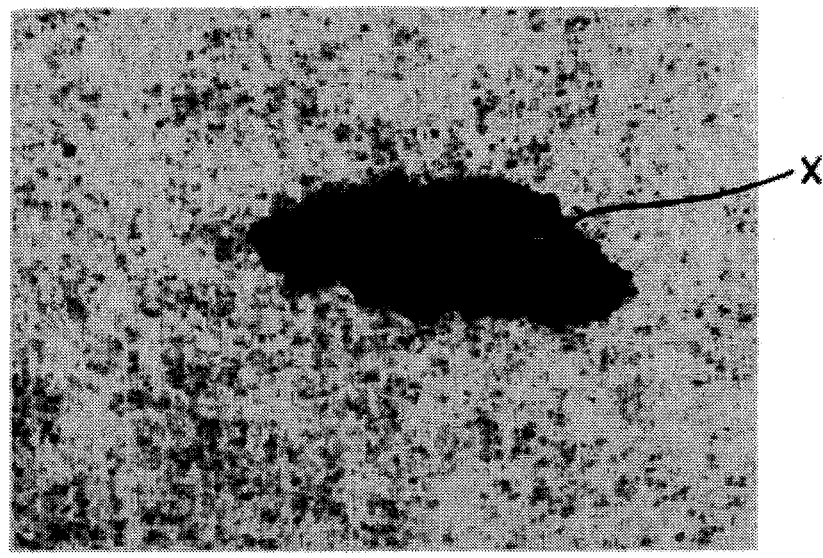

FIG. 12 is a photograph of the web of FIG. 10 at time=5 minutes.

Figure 13:
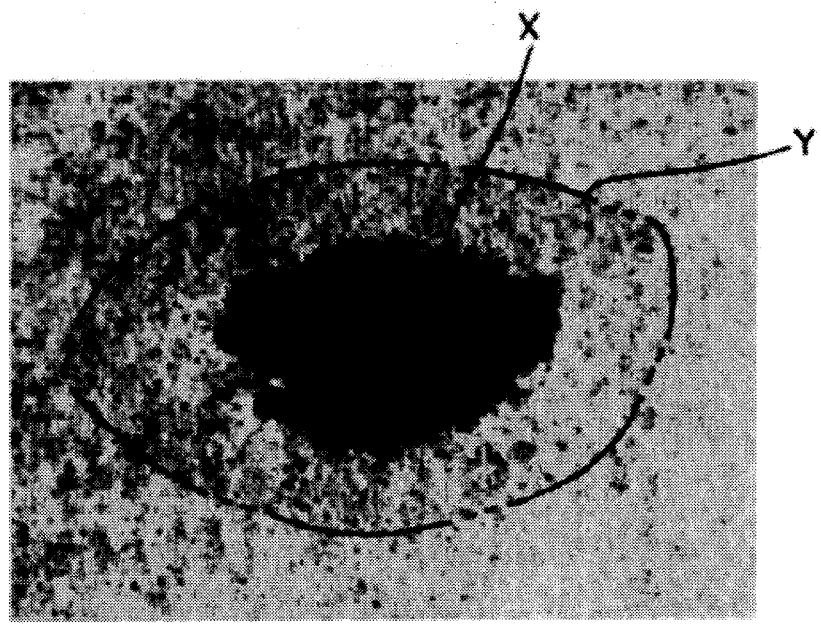

FIG. 13 is a photograph of the web of FIG. 11 at time=5 minutes.

As can be seen from reference to FIGS. 6–9, the control web (FIGS. 6 and 8) shows an area of interfiber fluid transport X but do not show any area of intrafiber fluid transport. The webs of shaped fibers (FIGS. 7 and 9) show an area of interfiber fluid transport X at time=5 seconds and 5 minutes and show an area of intrafiber fluid transport Y at time=5 minutes (FIG. 9).

As can be seen from reference to FIGS. 10–13, the control web (FIGS. 10 and 12) show an area of interfiber fluid transport X but do not show any area of intrafiber fluid transport. The web of shaped fibers (FIGS. 11 and 13) show an area of interfiber fluid transport X at time=5 seconds and 5 minutes and show an area of intrafiber fluid transport Y at time=5 minutes (FIG. 13).

Thus, it is seen that webs containing shaped fibers as described by the present invention are capable of intrafiber transport of a fluid. When a high-absorbency material is in liquid communication with the area of intrafiber fluid transport, the high-absorbency material is found to be at least partially swollen at time=5 minutes.

When liquid having a contact angle with the trilobal rayon of greater than 30 is substituted for the distilled water, no area Y of intrafiber liquid transport is formed in the tested webs.

The same general behavior is seen when the webs are subjected to a vertical wicking test wherein the test sample webs are suspended vertically above a container of distilled water containing a nonsubstantive dye with the end edges of the webs touching the water. Specifically, the webs formed from round fibers are found to vertically transport the water, through interfiber fluid transport, to a height of about 1.5–2.0 centimeters (time=5 minutes). The webs formed from trilobal rayon fibers are found to vertically transport the water, through interfiber fluid transport, to a height of about 1.5–2.0 centimeters and to vertically transport the water, through intrafiber fluid transport, to a height of about 5.5 centimeters (time=5 minutes).

While the present invention has been described in particular reference to several preferred embodiments, the present invention is susceptible of being embodied with various alterations and modifications which may differ particularly from those that have been described in the preceding specification. These variations and alterations are possible without departing from the described invention.

What is claimed is:

1. A nonwoven web for absorbing and transporting a liquid, said nonwoven web being capable of interfiber and intrafiber liquid transport, said nonwoven web comprising:

a shaped fiber, said shaped fiber defining a notch, said notch defining an angle alpha such that $\alpha<180$ degrees– $2\theta$ wherein $\theta$ is the contact angle between said liquid and said shaped fiber; and wherein said nonwoven web has a density of from about 0.01 gram per cubic centimeter to about 0.5 gram per cubic centimeter, and, further, whereby a liquid applied to said nonwoven web is subjected to interfiber liquid transport and to intrafiber liquid transport.

2. The nonwoven web according to claim 1 wherein said nonwoven web comprises at least about 25 weight percent of said shaped fiber based on the total weight of the nonwoven web.

3. The nonwoven web according to claim 2 wherein said nonwoven web comprises at least about 50 weight percent of said shaped fiber based on total weight of the nonwoven web.

4. The nonwoven web according to claim 1 wherein said nonwoven web comprises at least about 90 weight percent of said shaped fiber based on total weight of the nonwoven web.

5. The nonwoven web according to claim 1 wherein said nonwoven web comprises at least about 100 weight percent of said shaped fiber based on total weight of the nonwoven web.

6. The nonwoven web according to claim 1 wherein said shaped fiber is formed from a synthetic polymeric material.

7. The nonwoven web according to claim 1 wherein said shaped fiber is formed from a cellulose derivative.

8. The nonwoven web according to claim 1 wherein said shaped fiber defines two notches, each of said notches defining an angle alpha such that $\alpha<180°-2\theta$, wherein $\theta$ is the contact angle between said liquid and said shaped fiber.

9. The nonwoven web according to claim 8 wherein said shaped fiber defines three notches, each of said notches defining an angle alpha such that $\alpha<180°-2\theta$, wherein $\theta$ is the contact angle between said liquid and said shaped fiber.

10. The nonwoven web according to claim 1 wherein said shaped fiber has a diameter of from about 0.5 micrometer to about 40 micrometers.

11. The nonwoven web according to claim 1 wherein said nonwoven web has a density of from about 0.05 gram per cubic centimeter to about 0.2 gram per cubic centimeter.

12. A nonwoven web for absorbing and transporting a liquid, said nonwoven web being capable of interfiber and intrafiber liquid transport, said nonwoven web comprising:

a shaped fiber, said shaped fiber defining two notches, said notches defining an angle alpha such that $\alpha < 180$ degrees$-2\theta$, wherein $\theta$ is the contact angle between said liquid and said shaped fiber; and wherein said nonwoven web has a density of from about 0.05 gram per cubic centimeter to about 0.2 gram per cubic centimeter, and, further, whereby a liquid applied to said web is subjected to interfiber liquid transport and intrafiber liquid transport.

13. A disposable absorbent product capable of absorbing discharged body fluids, said absorbent product comprising:

a fluid-impervious outer cover;

a fluid-pervious bodyside liner adapted to contact the skin of a wearer, said bodyside liner being superposed on said outer cover; and an absorbent structure located between said outer cover and said bodyside liner, said absorbent structure comprising:

a nonwoven web for absorbing and transporting a liquid, said nonwoven web being capable of interfiber and intrafiber liquid transport and comprising a shaped fiber, said shaped fiber defining a notch, said notch defining an angle alpha such that $\alpha < 180° - 2\theta$, wherein $\theta$ is the contact angle between said liquid and said shaped fiber; and wherein said nonwoven web has a density of from about 0.01 gram per cubic centimeter to about 0.5 gram per cubic centimeter and, further, wherein a liquid applied to said nonwoven web is subjected to interfiber liquid transport and to intrafiber liquid transport.

14. The absorbent product according to claim 13 wherein said nonwoven web comprises at least about 25 weight percent of said shaped fiber based on the total weight of the nonwoven web.

15. The absorbent product according to claim 14 wherein said nonwoven web comprises at least about 50 weight percent of said shaped fiber based on the total weight of the nonwoven web.

16. The absorbent product according to claim 15 wherein said nonwoven web comprises at least about 90 weight percent of said shaped fiber based on the total weight of the nonwoven web.

17. The absorbent product according to claim 13 wherein said nonwoven web comprises about 100 weight percent of said shaped fiber based on the total weight of the nonwoven web.

18. The absorbent product according to claim 13 wherein said shaped fiber is formed from a synthetic polymeric material.

19. The absorbent product according to claim 13 wherein said shaped fiber is formed from a cellulose derivative.

20. The absorbent product according to claim 13 wherein said shaped fiber defines two notches, each of said notches defining an angle alpha such that $\alpha < 180° - 2\theta$, wherein $\theta$ is the contact angle between said liquid and said shaped fiber.

21. The absorbent product according to claim 20 wherein said shaped fiber defines three notches, each notch defining an angle alpha such that $\alpha < 180° - 2\theta$, wherein $\theta$ is the contact angle between said liquid and said shaped fiber.

22. A nonwoven web for absorbing and transporting a liquid, said nonwoven web having a density from about 0.01 gram per cubic centimeter to about 0.5 gram per cubic centimeter, said nonwoven web being capable of interfiber and intrafiber liquid transport.

\* \* \* \* \*